US010307106B2

(12) United States Patent
Wang et al.

(10) Patent No.: US 10,307,106 B2
(45) Date of Patent: Jun. 4, 2019

(54) SYSTEMS AND METHODS FOR ESTIMATING AND REMOVING MAGNETIC RESONANCE IMAGING GRADIENT FIELD-INDUCED VOLTAGES FROM ELECTROPHYSIOLOGY SIGNALS

(71) Applicants: BRIGHAM AND WOMEN'S HOSPITAL, INC., Boston, MA (US); UNIVERSITY OF GEORGIA RESEARCH FOUNDATION, INC., Athens, GA (US)

(72) Inventors: Wei Wang, Auburndale, MA (US); HuaLei Zhang, Brookline, MA (US); Ehud J. Schmidt, Newton, MA (US); Tsz Ho Tse, Lawrenceville, GA (US)

(73) Assignees: BRIGHAM AND WOMEN'S HOSPTIAL, INC., Boston, MA (US); UNIVERSITY OF GEORGIA RESEARCH FOUNDATION, INC., Athens, GA (US)

( * ) Notice: Subject to any disclaimer, the term of this patent is extended or adjusted under 35 U.S.C. 154(b) by 173 days.

(21) Appl. No.: 15/325,323

(22) PCT Filed: Jul. 10, 2015

(86) PCT No.: PCT/US2015/039874
§ 371 (c)(1),
(2) Date: Jan. 10, 2017

(87) PCT Pub. No.: WO2016/007816
PCT Pub. Date: Jan. 14, 2016

(65) Prior Publication Data
US 2017/0181709 A1    Jun. 29, 2017

Related U.S. Application Data

(60) Provisional application No. 62/023,313, filed on Jul. 11, 2014.

(51) Int. Cl.
*G01V 3/00* (2006.01)
*A61B 5/00* (2006.01)
(Continued)

(52) U.S. Cl.
CPC .......... *A61B 5/7217* (2013.01); *A61B 5/0402* (2013.01); *A61B 5/0476* (2013.01);
(Continued)

(58) Field of Classification Search
CPC .............. G01R 33/3415; G01R 33/543; G01R 33/5659; G01R 33/36; A61B 5/055
See application file for complete search history.

(56) References Cited

U.S. PATENT DOCUMENTS 4,991,587 A * 2/1991 Blakeley .............. A61B 5/0456
128/901
5,436,564 A   7/1995 Kreger et al.
(Continued)

OTHER PUBLICATIONS

The International Search Report and Written Opinion dated Oct. 1, 2015 for International Application No. PCT/US2015/039874.
(Continued)

*Primary Examiner* — Walter L Lindsay, Jr.
*Assistant Examiner* — Frederick Wenderoth
(74) *Attorney, Agent, or Firm* — Quarles & Brady LLP

(57) ABSTRACT

Systems and methods for estimating time-dependent voltages that are induced in electrophysiological monitoring systems by magnetic field gradients generated during a magnetic resonance imaging ("MRI") scan are provided. The gradient-induced voltages are subsequently removed from signals acquired with the electrophysiological monitoring system during an MRI scan. As an example, the electrophysiological monitoring system can include an electrocardiography ("ECG") system, an electroencephalography ("EEG") system, an electromyography ("EMG") sys-
(Continued)

tem, a voltage device tracking ("VDT") system, and so on. The gradient-induced voltages are estimated using a two-step procedure in which a learning algorithm is used to determine fitting parameters to be used in a model of the gradient-induced voltages. The fitting parameters are then used together with the model to extract the gradient-induced voltages from signals acquired during an MRI scan. The gradient-induced voltages can then be removed from the acquired signals.

14 Claims, 6 Drawing Sheets

(51) Int. Cl.
*G01R 33/567* (2006.01)
*A61B 5/0402* (2006.01)
*A61B 5/055* (2006.01)
*A61B 5/0476* (2006.01)
*A61B 5/0488* (2006.01)

(52) U.S. Cl.
CPC .......... *A61B 5/0488* (2013.01); *A61B 5/055* (2013.01); *G01R 33/5673* (2013.01); *A61B 5/725* (2013.01)

(56) References Cited

U.S. PATENT DOCUMENTS

| | | | |
|---|---|---|---|
| 6,025,715 A | 2/2000 | King et al. | |
| 2005/0265633 A1* | 12/2005 | Piacentino | G06T 5/50 382/302 |
| 2015/0139444 A1* | 5/2015 | Frazier | H04R 1/406 381/92 |

OTHER PUBLICATIONS

Felblinger et al., "Restoration of Electrophysiological Signals Distorted by Inductive Effects of Magnetic Field Gradients During MR Sequences," Magnetic Resonance in Medicine 41: 715-721 (1999), entire document. [online] [retrieved on Sep. 8, 2015]. Retrieved from the Internet: <URL: http://citeseerx.ist.psu.edu/viewdoc/download?doi=10.1.1.420.4957&rep=rep1&type=pdf>.

Extended European Search Report issued in corresponding European Application No. 15818236.0, dated Jan. 8, 2018, 8 pages.

Odille et al. "Noise Cancellation Signal Processing Method and Computer System for Improved Real-Time Electrocardiogram Artifact Correction During MRI Data Acquisition," IEEE Transactions on Biomedical Engineering, vol. 54, No. 4, Apr. 2007, pp. 630-640.

Zhang et al. "Computation of the gradient-induced electric field noise in 12-lead ECG traces during rapid MRI sequences," Journal of Cardiovascular Magnetic Resonance 2014, 16(Suppl 1):P151, 3 pages.

* cited by examiner

SYSTEMS AND METHODS FOR ESTIMATING AND REMOVING MAGNETIC RESONANCE IMAGING GRADIENT FIELD-INDUCED VOLTAGES FROM ELECTROPHYSIOLOGY SIGNALS

CROSS-REFERENCE TO RELATED APPLICATIONS

This application represents the national stage entry pf PCT International Application No. PCT/US2015/039874 filed on Jul. 10, 2015 and is based on, claims the benefit of, and incorporates herein in its entirety by reference U.S. Provisional Application Ser. No. 62/023,313, filed on Jul. 11, 2014, and entitled "SYSTEMS AND METHODS FOR ESTIMATING AND REMOVING MAGENTIC RESONANCE IMAGING GRADIENT FIELD-INDUCED VOLTAGES FROM ELECTROPHYSIOLOGY SIGNALS."

STATEMENT REGARDING FEDERALLY SPONSORED RESEARCH

This invention was made with government support under RR019703 and EB013873 awarded by the National Institutes of Health. The government has certain rights in the invention.

BACKGROUND OF THE INVENTION

The field of the invention is systems and methods for electrophysiology monitoring during magnetic resonance imaging ("MRI"). More particularly, the invention relates to systems and methods for removing magnetic gradient field-induced errors in electrophysiology signals (e.g., electrocardiogram, intracardiac electrocardiogram, electroencephalogram, electromyogram) acquired during the performance of an MRI pulse sequence.

When electrocardiograms ("ECG") traces are collected within the bore of a magnetic resonance imaging ("MRI") scanner while MRI images are being acquired, large induced voltages are superimposed on the conventional ECG traces. These voltages arise as a result of the MRI gradient coils, which induce large electrical fields into the human body, which then travel to the surface electrodes. These voltages can be 1000 times more intense than the native ECG (reaching up to 5V peak-to-peak), and as a result, it is frequently difficult to observe the physiologically-based ECG traces ("true ECG") during the execution of an MRI pulse sequence. This inability to observe the patient's true ECG traces restricts the ability to monitor the patient's physiology, or to properly synchronize the MRI scanner to the ECG, which is required in MRI sequences that are used to study the heart or the cardiovascular anatomy.

Removal of this MRI-gradient-induced voltage is currently (commercially) performed by a combination of several techniques. First, a restricted number (e.g., 4-6) of ECG electrodes are placed very close to each other, and at the center of the bore, in order to minimize the induced voltage. Second, high impedance (e.g., greater than 10 kΩ) transmission lines are typically used to reduce the amplitude of the currents that are generated by the gradient-induced voltages. Third, the received ECG traces are strongly low-pass frequency filtered so as to remove the higher frequency components of the induced voltages. Both of these operations results in ECG traces that are temporally distorted and very low in fidelity (i.e., low in amplitude with high noise content), so that they can be used only for synchronizing the MRI scanner, and not for monitoring the patient condition inside the MRI scanner. As a result, many severely-ill patients are excluded from MRI imaging and from MRI-guided surgical interventions.

For instance, most approaches apply strong low-pass filters of the order of 50 Hz to the ECG traces to remove the high-frequency components in the induced voltages. This approach is limited, however, by the retention of low frequency components of the gradient-induced voltages in the ECG traces, and it leads to distorted waveforms that are less useful for patient monitoring. Adaptive digital filter strategies have been used to reduce the ECG noise by detecting the gradient waveforms generated by the MRI pulse sequences and modeling the noise response as a linear time-invariant system that is convolved with the temporal response of the gradients. Most approaches have assumed that the time-derivates of the gradients are the major contributor, but a systematic derivation of the relationship between the gradients and the induced noise has not been demonstrated.

It would therefore be desirable to provide systems and methods that are capable of removing gradient-induced voltages from electrophysiology signal acquired during an MRI scan while preserving the pertinent information in the electrophysiology signals. For instance, such information may be used by clinicians to detect the onset and nature of several cardiac events to provide appropriate treatment.

SUMMARY OF THE INVENTION

The present invention overcomes the aforementioned drawbacks by providing a method for correcting electrophysiology signals by removing voltages induced by magnetic field gradients generated by a magnetic resonance imaging (MRI) system. The method includes providing gradient waveforms to be used by the MRI system and computing derivatives and other moments of the provided gradient waveforms. Electrophysiology signals are acquired from a subject positioned in the MRI system white the MRI system is generating magnetic field gradients based on the provided gradient waveforms. Fitting parameters for a physical model of the gradient-induced voltages are then estimated, and voltages induced by the generated magnetic field gradients are estimated by fitting the provided gradient waveforms, the computed derivatives and moments of the gradient waveforms, and the estimated fitting parameters to the physical model of gradient-induced voltages. The estimated gradient-induced voltages are then removed from the acquired electrophysiology signals.

The foregoing and other aspects and advantages of the invention will appear from the following description. In the description, reference is made to the accompanying drawings that form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Figure 1:
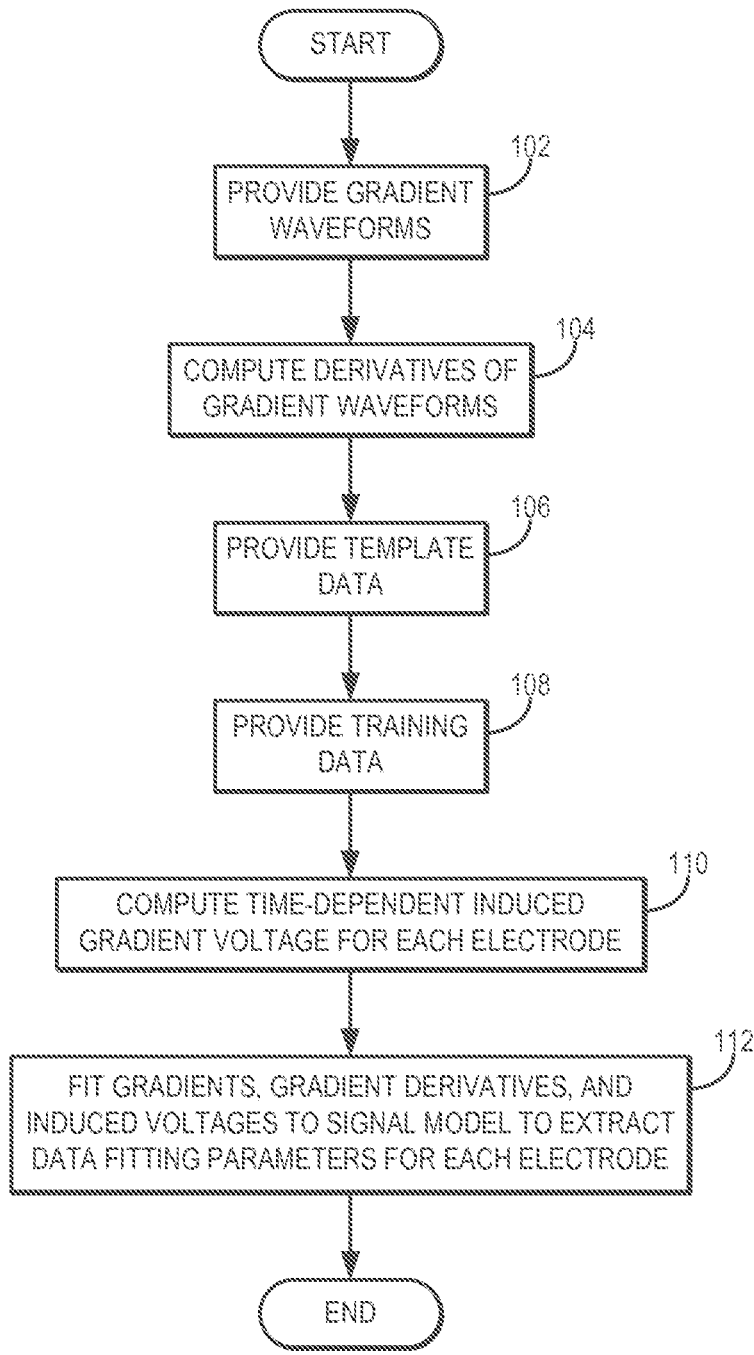
FIG. 1 is a flowchart setting forth the steps of an example method for estimating fitting parameters for a physical model of MRI gradient-induced voltages.

Described here are systems and methods for estimating time-dependent voltages that are induced in electrophysiological monitoring systems by magnetic field gradients generated during a magnetic resonance imaging ("MRI") scan, and subsequently removing the induced voltages from signals acquired with the electrophysiological monitoring system. As an example, the electrophysiological monitoring system can include an electrocardiography ("ECG") system, an intracardiac electrocardiogram ("EGM") system, an electroencephalography ("EEG") system, an electromyography ("EMG") system, and so on. The gradient-induced voltages are estimated using a two-step procedure in which a learning algorithm is used to determine fitting parameters to be used in a model of the gradient-induced voltages. The fitting parameters are then used together with the model to extract the gradient-induced voltages from signals acquired during an MRI scan. The gradient-induced voltages can then be removed from the acquired signals.

The model of the gradient-induced voltages is based on a physical description of the induced voltages, rather than an empirically-based equation. Using a physical model of the induced voltages results in very high-degree of agreement between the estimated voltage and the true, underlying gradient-induced voltage. The physical model, however, is based on several free parameters that are not known a priori. But, these free parameters can be learned or otherwise estimated using a learning algorithm or other suitable training-based estimation procedure.

Using the systems and methods of the present invention, the removal of the induced voltages does not reduce fidelity of the electrophysiological signals. For example, while running balanced Steady State Free Precession sequences with 3 ms repetition time, the 0-500 Hz frequency content of the electrophysiological signals can be retained to keep the full diagnostic fidelity of the ECG signals, thereby allowing the signals to be used for physiological monitoring.

The systems and methods of the present invention can be utilized in a range of different applications, including MRI-compatible voltage-device-tracking ("VDT"), whereby electrical signals, which can be in the KHz frequency range, are used for both measuring the voltages in vivo and for spatial localization of an interventional device, such as a catheter or other device. These methods include directing electrical pulses into the subject's body and detecting the resulting signals using electrodes positioned on the interventional device. In this example, the systems and methods of the present invention can enable electro-anatomical mapping ("EAM") during MRI imaging, which includes mapping the locations contacted by the catheters along with electrical activity thereby.

In some embodiments, the systems and methods of the present invention can be used to remove voltages induced by MRI gradient fields in 12-lead ECG systems when acquiring data using a high-duty-cycle MRI pulse sequence. As discussed above, electrophysiology systems other than ECG systems can also benefit from the present invention. In this manner, true ECG traces can be observed while the MRI is acquiring images. In some instances, for these high-duty-cycle pulse sequences, a minimal amount of blanking (i.e., blocking of electrical signals received when gradient fields are being generated) can be employed to remove the strongest induced voltages, whose temporal timing can be predicted using the methods described here. Otherwise, the induced voltages are acquired by the ECG receiver and later removed using the systems and methods described here.

To preserve the fidelity of the true 12-lead ECG traces, low-pass filters are not used to remove the induced voltages; instead, the induced voltages are modeled using electromagnetic ("EM") principles. Using this physical model approach results in a mathematical equation that governs the time course of the induced-voltage, based on the gradient-waveform that is played out at each time point. One example of an equation that can be used to model the induced voltage, $V_k$, at each of k different electrodes used in the 12-lead ECG measurement is, $$V_k(t) = \alpha_k \frac{\partial G_x}{\partial t} + \beta_k \frac{\partial G_y}{\partial t} + \gamma_k \frac{\partial G_z}{\partial t} + \delta_k G_x(t) + \varepsilon_k G_y(t) + \zeta_k G_z(t) + C_k; \quad (1)$$

where $G_x$ is a gradient waveform for a magnetic field gradient established in the x-direction; $G_y$ is a gradient waveform for a magnetic field gradient established in the y-direction; $G_z$ is a gradient waveform for a magnetic field gradient established in the z-direction; $\alpha_k$, $\beta_k$, $\gamma_k$, $\delta_k$, $\varepsilon_k$ and $\zeta_k$ are free parameters that depend on the magnetic gradient waveforms; and $C_k$ is a free parameter that does not depend on the gradient waveforms, but which accounts for receiver temporal non-linearities.

Another example of an equation that can be used to model the induced voltage, $V_k$, at each of K different electrodes used in the 12-lead ECG measurement is, $$V_k(t) = p_{1k} \frac{\partial G_x}{\partial t} + p_{2k} \frac{\partial G_y}{\partial t} + p_{3k} \frac{\partial G_z}{\partial t} + p_{4k} G_x + p_{5k} G_y + \quad (2)$$
$$p_{6k} G_z + p_{7k} \frac{\partial G_x}{\partial t} G_x + p_{8k} G_x^2 + p_{9k} \frac{\partial G_y}{\partial t} G_y + p_{10k} G_y^2 +$$
$$p_{11k} \frac{\partial G_z}{\partial t} G_z + p_{12k} G_z^2 + p_{13k} \frac{\partial G_x}{\partial t} G_z + p_{14k} \frac{\partial G_z}{\partial t} G_x +$$
$$p_{15k} G_x G_z + p_{16k} \frac{\partial G_y}{\partial t} G_z + p_{17k} \frac{\partial G_z}{\partial t} G_y + p_{18k} G_y G_z + C_k.$$

where $P_{1k}$, ..., $P_{18k}$ are free parameters that depend on the magnetic gradient waveforms; and $C_k$ is a free parameter that does not depend on the gradient waveforms, but which accounts for receiver temporal non-linearities The additional terms $P_{7k}$-$P_{18k}$ in the physical model in Eqn. (2) are cross terms and $p_{13k}$-$p_{18k}$ only exist when gradient fields are established along more than one direction at a time. It is a discovery that these additional terms have significant contributions in the relatively-high gradient-induced voltages seen in electrodes placed farther away from the magnet iso-center, such as the limb leads in an ECG system. It should be noted that in both Eqns. (1) and (2), additional free parameters beyond $C_k$ can be included in the model of gradient-induced voltages to better account for temporal non-linearities, such as accounting for "ring downs," which occur immediately after the reception of very strong input signals. For example, higher order parameters can be incorporated into the models, which may include higher order time-dependent components such as $C_{1k}t$ and $C_{2k}t^2$, where $C_{1k}$ and $C_{2k}$ are electrode-specific constants and t is time.

The physical models of the gradient-induced voltages in Eqns. (1) and (2) have multiple free parameters that are specific to the given patient, the position and quality of the ECG-electrodes, the pulse sequence used, and the pulse-sequence-orientation. These constants are not known a priori; thus, they must be learned or otherwise estimated so the appropriate physical model can be used to remove the gradient-induced voltages from the ECG traces.

Referring now to FIG. 1, a flowchart setting forth the steps of an example method for estimating the fitting parameters for the physical model of the gradient-induced voltages is illustrated. The method includes providing the gradient waveforms that will be used during the actual data acquisition, as indicated at step 102. For instance, the three gradient waveforms can be simultaneously collected, digitized, and stored. As one example, the gradient waveforms can be measured by connecting three analog-to-digital converters ("ADCs") to the gradient subsystem, or "cabinet," of the MRI system, and by sampling the three waveforms. Preferably, the gradient waveforms are sampled at a high temporal resolution, such as 40-60 kilo-samples per second, and using a large dynamic range (e.g., approximately one million) because the gradient-induced voltages can reach amplitudes of 10 Volts, whereas fidelity standards for physiological monitoring requires noise levels of approximately 10 microVolts. The derivatives of the provided gradient waveforms are then computed, as indicated at step 104. However, other moments of the gradient waveforms may also be computed at step 104, for instance as described with reference to Eqn. 2, including squares of the gradient components, cross-terms of the gradient components, and so forth.

Figure 2:
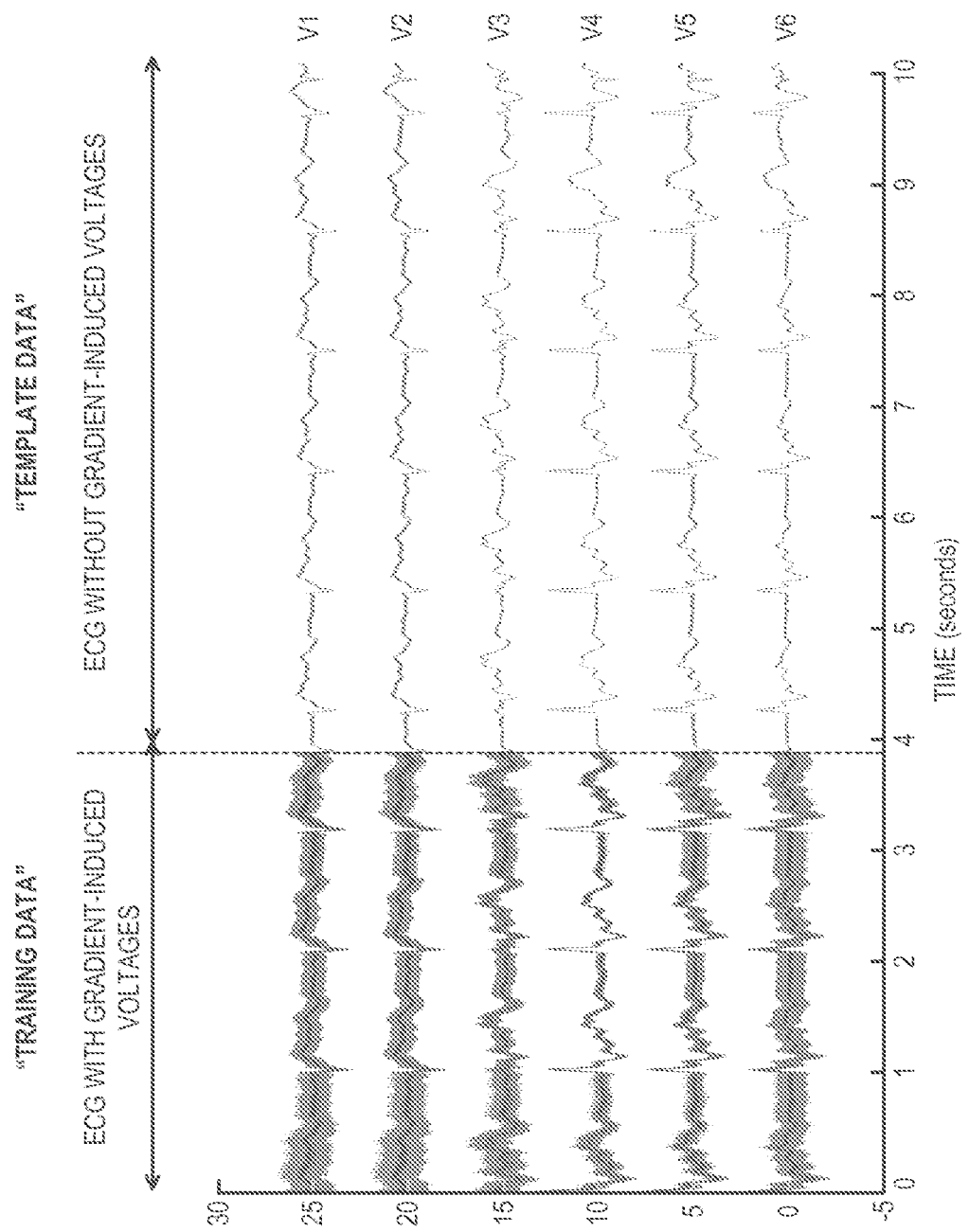
FIG. 2 is a plot illustrating example training data and template data of precordial ECG channels V1-V6.

Template data and training data are provided next, as indicated at steps 106 and 1013, respectively. The template data includes electrophysiology signals acquired in the absence of magnetic field gradients. As such, the template data contains no gradient-induced voltages, but instead is representative of the "true" signal. As an example, the template data can be acquired by sampling the electrophysiology traces alone for a short time when the MRI system is not pulsing. The training data includes electrophysiology signals acquired in the presence of magnetic field gradients generated using the provided gradient waveforms. As such, the training data includes gradient-induced voltages. Examples of training data can be seen in the left-hand side of FIG. 2, and examples of template data can be seen in the right-hand side of FIG. 2.

As an example, the training data can be acquired while performing a condensed form of the MRI pulse sequence that will be used during actual data acquisition. For instance, the training segment can utilize an "accelerated form" of the MRI pulse sequence using parallel imaging methods, such as GRAPPA or SENSE. The advantages of these accelerated sequences is that they possess the full dynamic-range of the MRI-gradient waveforms that are used in the ordinary (i.e., non-accelerated) MRI pulse sequence, such as the full range of phase-encoding steps, but they move between this range in a far shorter time.

The template data and training data are then used to compute an estimate of the time-dependent gradient-induced voltage for each electrode, as indicated at step 110. As an example, this processing may include computing the true electrophysiology signal from the template data. For instance, if the electrophysiology signal is an ECG signal, computing the true ECG signal may include computing the true ECG waveform ("ECG template") for a complete R-R cycle for each electrode by averaging the sampled true ECG over a few cardiac cycles. This processing may also include finding the position of the QRS complexes in the corrupted ECGs contained in the training data. The time-dependent gradient-induced voltage can then be estimated by subtracting the ECG template from the corrupted ECG for each given electrode, thereby obtaining a time course of the gradient-induced voltage for that electrode.

The computed time-dependent gradient-induced voltage for each electrode is then fit to the physical model of the gradient-induced voltage to obtain the fitting parameters for the particular gradient waveforms and subject, as indicated at step 112. For instance, the time-dependent gradient-induced voltage for each electrode can be fit to the model in Eqn. (1).

Figure 3:
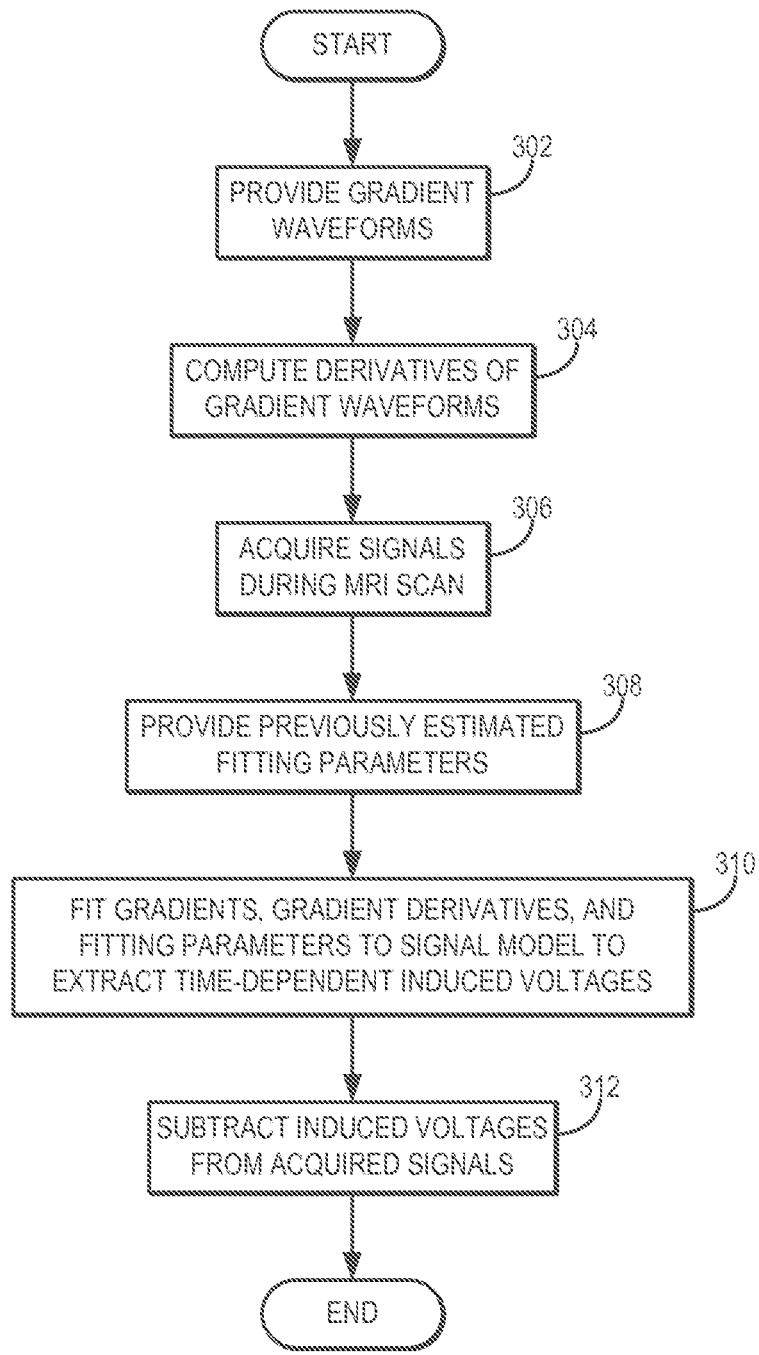
FIG. 3 is a flowchart setting forth the steps of an example method for estimating and removing MRI gradient-induced voltages from electrophysiology signals acquired during the performance of an MRI scan.

Referring now to FIG. 3, a flowchart setting forth the steps of a method for estimating and removing gradient-induced voltages from electrophysiology signals acquired during the performance of an MRI scan is illustrated. The method includes providing the gradient waveforms that will be used during the MRI scan, as indicated at step 302. The derivatives of these gradient waveforms are also provided or otherwise calculated, as indicated at step 304. As described, other moments of the gradient waveforms may also be provided or calculated at step 304.

Electrophysiology signals are then acquired during the performance of an MRI pulse sequence, as indicated at step 306. In some embodiments, the electrophysiology signals are previously acquired in this manner and are provided for processing. The fitting parameters estimated using the training data are then provided, as indicated at step 308. In some embodiments, the training procedure is not required; instead, the fitting parameters can be estimated from the acquired electrophysiology signals using an adaptive filtering technique to iteratively resolve the fitting parameters.

Figure 4:
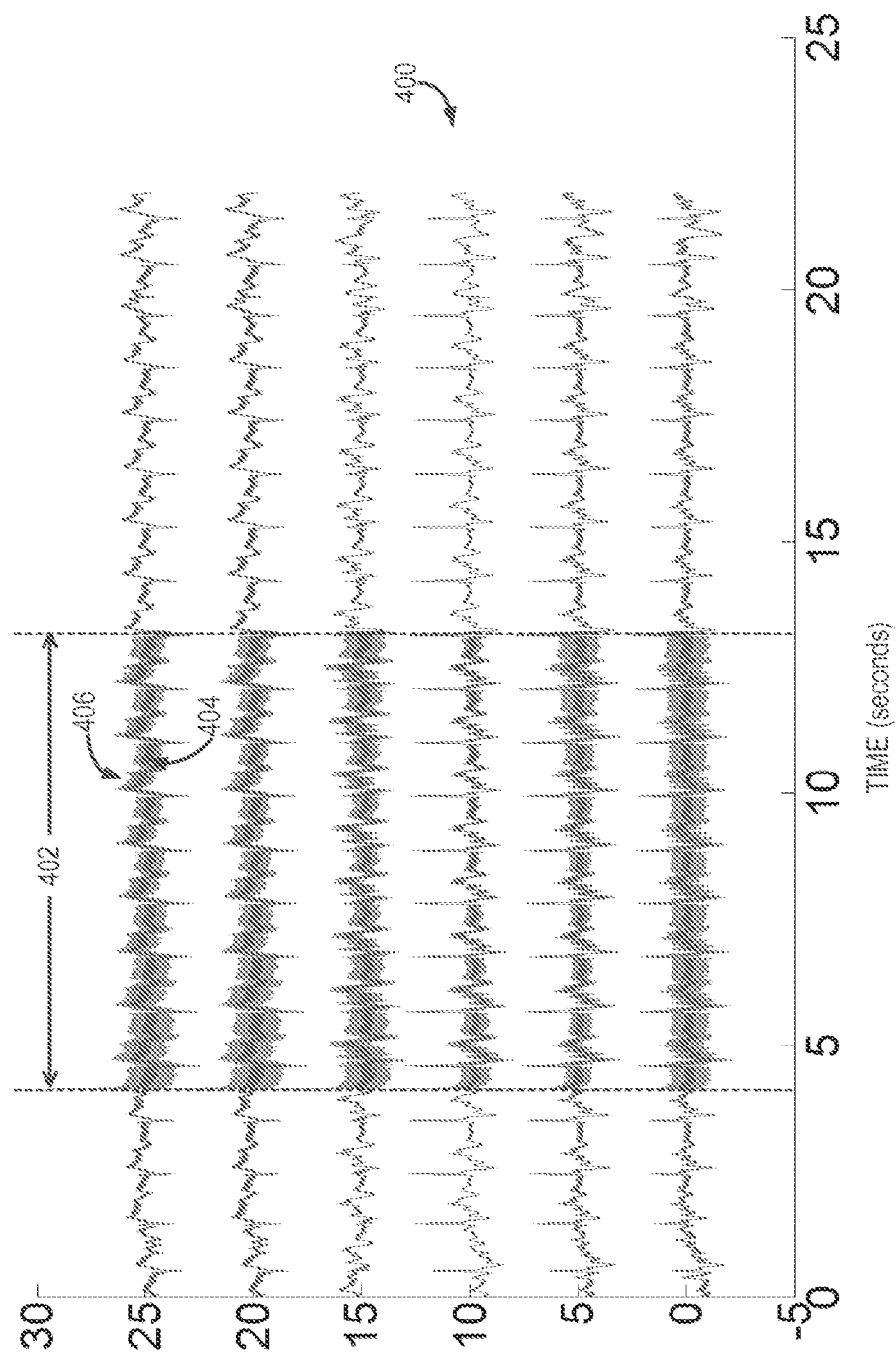
FIG. 4 is a plot illustrating example ECG traces corrected for gradient-induced voltages.

The time-dependent gradient-induced voltages present in the acquired electrophysiology signals are then estimated as indicated at step 310. As an example, the gradient waveforms, derivatives of the gradient waveforms, and estimated fitting parameters are fit to the physical model of the gradient-induced voltages to estimate the gradient-induced voltages present in the acquired electrophysiology signals. The estimated gradient-induced voltages can then be removed from the acquired electrophysiology signals, as indicated at step 312. For instance, the gradient-induced voltages can be subtracted from the acquired electrophysiology signals. Using this technique, the gradient-induced voltages can be removed in "real-time" with a significantly low latency time of a few milliseconds, and the true signal traces can be displayed. By way of example, FIG. 4 illustrates ECG traces 400 acquired from a subject positioned in an MRI system over a time period which includes application of gradients. Specifically, during the gradient time period 402, the restored 404 ECG traces, in accordance with methods described herein, exhibit appreciably different noise profiles compared to the raw 406 ECG traces. As described, the restored 404 ECG traces may be computed, and displayed, in substantially real-time, using fitted parameters from a training stage.

Figure 5:
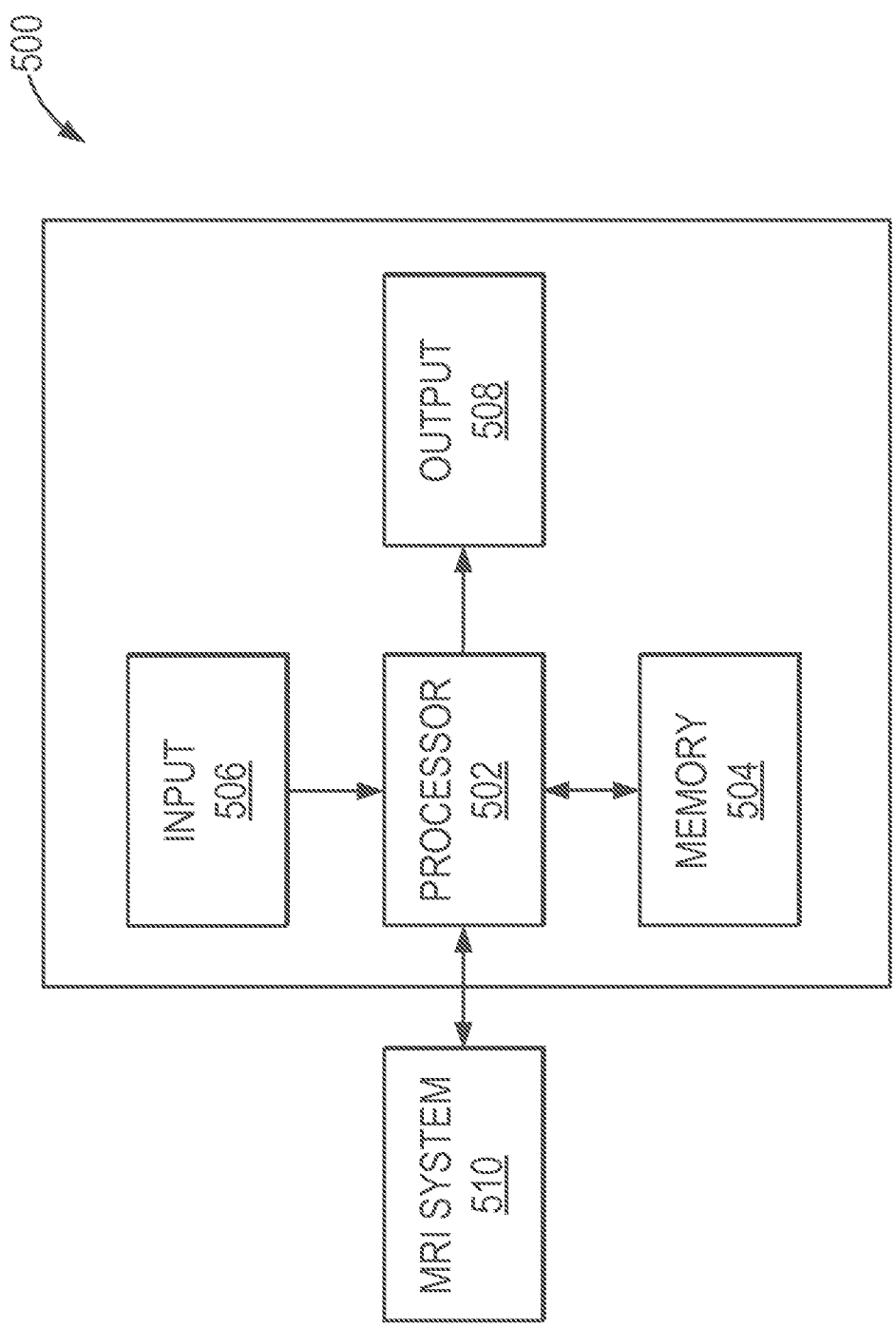
FIG. 5 is a diagram for an example system in accordance with aspects of the present disclosure.

Turning to FIG. 5, a block diagram of a system 500, for use in accordance with the present disclosure, is illustrated. In some configurations, the system 500 can include a processor 502, a memory 504, an input 506, an output 508, and may be configured to carry out steps, in accordance with methods described herein, including estimating and correcting acquired electrophysiology signals by removing voltages induced by magnetic field gradients generated by a magnetic resonance imaging (MRI) system 510.

In some implementations, system 500 may be an electrophysiological monitoring system, such as an electrocardiography ("ECG") system, an electroencephalography ("EEG") system, an electromyography ("EMG") system, a voltage device tracking ("VDT") system, and so on, configured to communicate with an MRI system 510, or subsystem therein, as shown in FIG. 5. In other implementations, system 500 may be part of an MRI system.

In general, the system 500 may be any device, apparatus or system configured for carrying out instructions for, and may operate as part of, or in collaboration with a computer, system, device, machine, mainframe, or server. In this regard, the system 500 may be a system that is designed to integrate with a variety of software and hardware capabilities and functionalities, and may be capable of operating autonomously. In some aspects, the system 500 may be portable, such as a mobile device, tablet, or other portable device or apparatus. In addition, in some configurations, the system 500 may also include or be used in cooperation with an interventional device or apparatus configured for carrying out a medical procedure.

In addition to being configured to carry out steps for operating the system 500 using instructions stored in the memory 504, the processor 502 may be configured to acquire and process electrophysiological signals, such as ECG signals, from a subject positioned in the MRI system. As described, such electrophysiology signals may be acquired either while the MRI system is generating magnetic field gradients, or while the MRI system is not generating magnetic field gradients, or both. In some aspects, the processor 502 may pre-process or modify the acquired signals, including carrying out steps for filtering, integrating, amplifying, time-delaying, and so forth, the signals.

In accordance with aspects of the present disclosure, the processor 502 may he programmed to carry out steps for correcting acquired electrophysiology signals by removing voltages induced by the magnetic field gradients generated by the MRI system. Specifically, the processor 502 may receive gradient waveforms and other data, for example, via input 506 or directly from the MRI system 510, and compute derivatives, and other moments, for the received gradient waveforms. The processor 502 may then estimate fitting parameters for a physical model of gradient-induced voltages, as described, and estimate the voltages induced by the generated magnetic field gradients by fitting the provided gradient waveforms, the computed derivatives of the gradient waveforms, and the estimated fitting parameters to the physical model of gradient-induced voltages. In some aspects, fitting parameters may he retrieved by the processor 502 from the memory 504 or other storage device, having been estimated and stored during a training stage. The estimated gradient-induced voltages may then be removed from the acquired electrophysiology signals by the processor 502. The corrected or restored electrophysiology signals may then be included in a report to a clinician, along with any other data or information, provided via the output 508, for example, in the form of a display, either intermittently or in substantially real-time.

Figure 6:
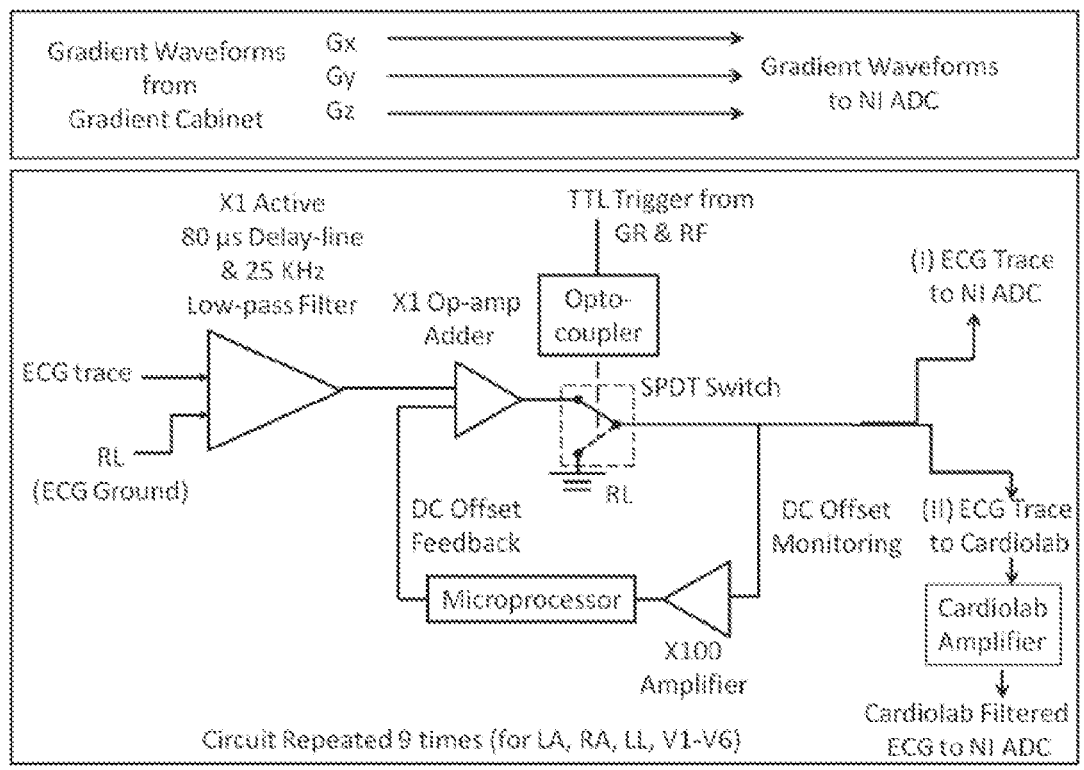
FIG. 6 is a diagram of an example MRI-compatible 12-lead ECG front end that enables patient-isolation via a differential pre-amp/delay-line at its input, and allows for blocking strong signals via a transistor-transistor logic ("TTL")-controlled single pole double throw ("SPDT") switch, and also allows sampling of the full amplitude and spectral content of the traces acquired while the MRI system is pulsing.

Referring now to FIG. 6, a diagram is shown illustrating an example of an MRI-compatible 12-lead ECG front end that can be used when practicing some embodiments of the present invention. In this example configuration, each ECG channel, including the pre-cordial leads V1-V6 and the limb leads (i.e., Right-Arm ("RA") Left-Leg ("LL") and Left-Arm ("LA") leads), enters the system via a TTE AL181-25k-179A (Los Angeles, Calif.) unity-gain differential amplifier/delay-line, with the Right-Leg ("RL") input acting as the reference voltage. This TTE unit utilizes a 10-pole Chebyshev filter to provide an 80-microsecond signal delay and a 25 kHz low-pass frequency. This unit provides adequate impedance matching between the human body and the front-end electronics, preserving linear-phase unity-gain ECG traces without any signal corruption and attenuation. An Analog Devices (Norwood, Mass.) AD8674 low-noise op-amp adder was placed before the single pole double throw (SPDT) switch, in order to correct for DC offsets introduced by the delay-line low-pass filter and the SPDT switch during gradient noise blanking. The front-end ECG analog output was acquired with a National Instruments (NI) CompactRio microprocessor (Austin, Tex.) for DC offset monitoring. A feedback loop, with the feedback voltage controlled by the microprocessor that measured the resulting DC offset, removed most of the DC offsets (down to 0.05 mV) produced by the switch and the delay-line low-pass filter.

In some configurations, in order to measure the full spectrum of the ECG signal as well as the gradient-induced noise superimposed on the ECG signals, the circuit output can be sent directly to a National Instruments PCI-6251 Analog-to-Digital Converter (ADC), which digitizes the ECG waveforms at a rate of 48 kHz. The maximum input voltage of the NI ADC can be set at +10 Volts, so none of the ECG traces are clipped. As noted above, all measurements can be referenced to the RL lead.

In some other configurations, in order to measure the ECG spectrum as it appears after filtering, the circuit output can also be sent to a digital ECG recording system, such as a GE Cardiolab IT (Waukesha, Wis.) system. As an example, the digital ECG recording system can apply Butterworth 1st-order 0.05 Hz high-pass & 3rd-order 100 Hz low-pass filters to the ECG traces. In the Cardiolab digital ECG recording systems, the amplifier gain can be set to either 1000 or 100, which allows precordial leads to be acquired without saturation. The Cardiolab pre-processing and larger-input gain is capable of achieving a maximum input amplitude of ~10 mV peak-to-peak (after the hardware filtering), so that all the limb leads and several V6 recordings performed during imaging can be saturated. The ECG traces can be output from the Cardiolab system in analog form and re-digitized by the NI ADC. All measurements can be referenced to the RL lead. The x, y and z gradient waveforms can be transmitted from the MRI gradient cabinet and digitized by the NI ADC card simultaneously with the ECG traces.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for correcting electrophysiology signals by removing voltages induced by magnetic field gradients generated by a magnetic resonance imaging (MRI) system, the steps of the method comprising:

(a) providing gradient waveforms;
(b) computing derivatives of the provided gradient waveforms;
(c) acquiring electrophysiology signals from a subject positioned in the MRI system while the MRI system is generating magnetic field gradients based on the provided gradient waveforms;
(d) estimating fitting parameters for a physical model of gradient-induced voltages;
(e) estimating voltages induced by the generated magnetic field gradients by fitting the provided gradient waveforms, the computed derivatives of the gradient waveforms, and the estimated fitting parameters to the physical model of gradient-induced voltages;
(f) removing the estimated gradient-induced voltages from the acquired electrophysiology signals to produce corrected electrophysiology signals; and
(g) displaying the corrected electrophysiological signals on a display.

2. The method as recited in claim 1, wherein step (d) includes estimating the fitting parameters by adaptively filtering the acquired electrophysiology signals.

3. The method as recited in claim 1, wherein step (d) includes estimating the fitting parameters by:
(i) providing an estimate of gradient-induced voltages associated with the provided gradient waveforms; and
(ii) fitting the provided gradient waveforms, the computed derivatives of the gradient waveforms, and the estimate of the gradient-induced voltages to the physical model of the gradient-induced voltages.

4. The method as recited in claim 3, wherein providing the estimate of gradient-induced voltages includes:
(i) providing training electrophysiology signal data acquired from the subject while the MRI system is generating magnetic field gradients based on the provided gradient waveforms;
(ii) providing template electrophysiology signal data acquired from the subject while the MRI system is not generating magnetic field gradients; and
(iii) computing the estimate of gradient-induced voltages based on the provided training electrophysiology signal data and the provided template electrophysiology signal data.

5. The method as recited in claim 4, wherein computing the estimate of gradient-induced voltages includes subtracting the training electrophysiology signal data and the template electrophysiology signal data.

6. The method as recited in claim 4, wherein the provided template electrophysiology signal data is the electrophysiology signal data acquired in step (c).

7. The method as recited in claim 1, wherein the electrophysiology signals include at least one of electrocardiography (ECG) signals, intracardiac electrocardiogram (EGM) signals, electroencephalography (EEG) signals, electromyography (EMG) signals, voltage device tracking (VDT) signals, or a combination thereof.

8. A system for correcting electrophysiology signals affected by magnetic field gradients generated by a magnetic resonance imaging (MRI) system, the system comprising:
an input configured to receive electrophysiology signals acquired from a subject positioned in an MRI system;
at least one processor configured to:
  i) to receive gradient waveforms from the input;
  ii) compute derivatives of the received gradient waveforms;
  iii) estimate fitting parameters for a physical model of gradient-induced voltages;
  iv) estimate voltages induced by the generated magnetic field gradients by fitting the gradient waveforms, the computed derivatives of the gradient waveforms, and the estimated fitting parameters of the physical model of gradient-induced voltages;
  v) remove the estimated gradient-induced voltages from the acquired electrophysiology signals to produce corrected electrophysiology signals; and
  vi) generate a report using the corrected electrophysiology signals.

9. The system as recited in claim 8, wherein the at least one processor is further configured to estimate the fitting parameters by adaptively filtering the acquired electrophysiology signals.

10. The system as recited in claim 9, wherein the at least one processor is further configured to estimate the fitting parameters by:
a) providing an estimate of gradient-induced voltages associated with the provided gradient waveforms; and
b) fitting the provided gradient waveforms, the computed derivatives of the gradient waveforms, and the estimate of the gradient-induced voltages to the physical model of the gradient-induced voltages.

11. The system as recited in claim 10, wherein the at least one processor is configured to provide the estimate of gradient-induced voltages by:
a) providing training electrophysiology signal data acquired from the subject while the MRI system is generating magnetic field gradients based on the provided gradient waveforms;
b) providing template electrophysiology signal data acquired from the subject while the MRI system is not generating magnetic field gradients; and
c) computing the estimate of gradient-induced voltages based on the provided training electrophysiology signal data and the provided template electrophysiology signal data.

12. The system as recited in claim 11, wherein computing the estimate of gradient-induced voltages including subtracting the training electrophysiology signal data and the template electrophysiology signal data.

13. The system as recited in claim 11, wherein the at least one processor is further configured to direct acquisition of the electrophysiology signals from the subject to generate the training electrophysiology signal data, the template electrophysiology signal data, or both.

14. The system as recited in claim 8, wherein the electrophysiology signals include at least one of electrocardiography (ECG) signals, intracardiac electrocardiogram (EGM) signals, electroencephalography (EEG) signals, electromyography (EMG) signals, voltage device tracking (VDT) signals, or a combination thereof.

* * * * *